United States Patent [19]

Klieman et al.

[11] 4,188,953
[45] Feb. 19, 1980

[54] HEMOSTATIC CLIP

[75] Inventors: Charles H. Klieman, 3737 Century Blvd., Lynwood, Calif. 90262; Richard M. Densmore, South Gate, Calif.

[73] Assignee: Charles H. Klieman, M.D., Los Angeles, Calif.

[21] Appl. No.: 822,095

[22] Filed: Aug. 5, 1977

[51] Int. Cl.² .............................................. A61B 17/12
[52] U.S. Cl. ...................................... 128/325; 128/346; 24/22
[58] Field of Search ............... 128/325, 326, 346, 321, 128/322, 337, 354; 251/9, 10; 24/20 S, 22, 24, 115 A, 129 W, 248 R, DIG. 22, 30.5 W, 95, 97; 269/257, 271, 279

[56] References Cited

U.S. PATENT DOCUMENTS

| | | | |
|---|---|---|---|
| 2,598,901 | 6/1952 | Garland | 24/30.5 W X |
| 3,270,745 | 9/1966 | Wood | 128/325 |
| 3,363,628 | 1/1968 | Wood | 128/325 |
| 3,766,926 | 10/1973 | Bliss | 128/325 X |
| 3,867,944 | 2/1975 | Samuels | 128/334 R X |

FOREIGN PATENT DOCUMENTS 529,919  12/1921  France ...................... 128/322

*Primary Examiner*—Henry J. Recla
*Attorney, Agent, or Firm*—Spensley, Horn, Jubas & Lubitz

[57] ABSTRACT

A hemostatic clip useful in the strangulation of tubular members and formed of elongate deformable material is disclosed. The clip consists of a pair of arms coupled at one end and open at the other, the arms being separated in a substantially opposed relationship and each having a flat surface facing inwardly. Located in the flat surfaces of the arms are diagonal recesses. The recesses in opposing surfaces are arranged so as to be angularly displaced with respect to one another such that when the surfaces are brought into contact the recesses on opposing surfaces form a cross-hatched pattern.

2 Claims, 9 Drawing Figures

HEMOSTATIC CLIP

BACKGROUND OF THE INVENTION

1. Copending Pat. Applications

In copending U.S. Pat. application Ser. No. 822,096 entitled SURGICAL STAPLER filed Aug. 5, 1966, and in copending U.S. patent application Ser. No. 822,076 entitled HEMOSTATIC CLIP APPLICATOR filed Aug. 5, 1977, both assigned to the present assignee, hemostatic clip applicators for the strangulation of tubular members in a rapid and automatic manner is disclosed. The present invention is directed toward hemostatic clips useful in the above cited devices and similar applying devices.

2. Field of the Invention:

The invention relates to the field of devices useful in the strangulation of tubular members, and more specifically, to hemostatic clips used in the strangulation of blood vessels and other fluid ducts.

3. Prior Art:

Many surgical procedures require the severence and closure of numerous veins, arteries or other blood vessels and fluid ducts. Typically, this severence and closure has been accomplished by first severing the vessel and then clamping it with a hemostat. A ligature is then secured about each vessel which provides closure and permits removal of the clamps. This procedure is quite time consuming and some surgical procedures are further complicated by the fact that they require the closure of a great many vessels in a very limited area.

One prior art attempt to provide more rapid yet effective strangulation of blood vessels and the like is described by Skold, U.S. Pat. No. 3,120,230. Skold utilizes a clip formed from a length of smooth round wire stock which has been bent into a generally V-shaped configuration. This length of wire is squeezed around the vessel, which is to be closed, by an application device. Another prior art attempt to provide effective strangulation is described by Samuels, U.S. Pat. No. 3,867,944. The clip disclosed by Samuels is also a generally V-shaped configuration, although it has teeth-like projections extending inwardly on two opposing arms. When the clip is closed about a vessel, the opposing teeth of the clip engaged the vessel from both sides and squeeze it shut. A third prior art attempt to provide rapid yet effective strangulation is disclosed by Wood, U.S. Pat. No. 3,363,628. The Wood clip is formed of a strip of non-toxic material which is triangular in cross-section, having a flat side facing inwardly and at least one valley along the outer length of the material. Across the flat inwardly facing sides are serations configured so as to run parallel to the direction of the vessel. A fourth prior art attempt to provide an effective clip design is disclosed by Wood, U.S. Pat. No. 3,326,216. This Wood clip is also formed of an elongate strip of non-toxic material which has at least one longitudinal valley and at least one crosswise serration in the interior surface of its pair of arms.

Two problems are associated with all of the prior art clip constructions noted above. First, the surface area of contact between the opposing faces of the clips is severely limited by the configuration of the faces. This limited surface area could prevent thorough strangulation, resulting in the possibility of incomplete closure. Second, the configuration of the surface areas which contact the vessel allow possible slippage of the clip along the vessel. That is, the surface areas contacting the vessel are configured such that they do not oppose slippage of the clip along the length of the vessel being secured.

Accordingly, it is a general object of the present invention to provide an improved hemostatic clip for the strangulation of blood vessels and the like.

It is another object of the present invention to provide an improved hemostatic clip with a large surface area of contact between the opposing surfaces of the clips.

It is yet another object of the present inveniton to provide an improved hemostatic clip which will not slip along the length and width of the vessel.

SUMMARY OF THE INVENTION

A hemostatic clip useful for strangulation of blood vessels and the like is provided. The clip has a pair of arms coupled at one end to a bail portion and open at the other, each arm having a substantially flat surface facing inwardly. In each flat surface are a multiple of recesses, having a V-shaped cross-section, which extend diagonally across each surface. The diagonal recesses are arranged in the opposing flat surfaces so that when the surfaces are brought into contact by squeezing the clip together the recesses in the opposing surfaces form a generally cross-hatched pattern. The bail portion of the clip has a substantially rectangular cross-section, while the arm portions are generally hexagonal in cross-section.

The novel features which are believed to be characteristic of the invention, both as to its organization and its method of operation, together with further objects and advantages thereof, will be better understood from the following description in connection with accompanying drawings in which a presently preferred embodiment of the invention is illustrated by way of example. It is to be expressly understood, however, that the drawings are for purposes of illustration and description only and are not intended as a definition of the limits of the invention.

DETAILED DESCRIPTION OF THE INVENTION

A hemostatic clip is disclosed which is useful in the strangulation of blood vessels and other fluid ducts. The hemostatic clip of the present invention may be used with an applicator device such as is described in our copending application Ser. No. 822,096, filed on Aug. 5, 1977, entitled "Surgical Stapler", or in our copending application Ser. No. 822,076 filed on Aug. 5, 1977, entitled HEMOSTATIC CLIP APPLICATOR or in any other suitably adapted applicator device.

In the presently preferred embodiment, the hemostatic clip is formed from tantalum, although any other deformable, non-toxic, biologically inert material such as stainless steel, plastics and materials which are slowly absorbed in body fluids may also be used, provided such material generally retains the shape to which it is deformed. The utilization of the materials noted above allow the hemostatic clip of the present invention to be tolerated in the body for indefinite periods of time.

Figure 1:
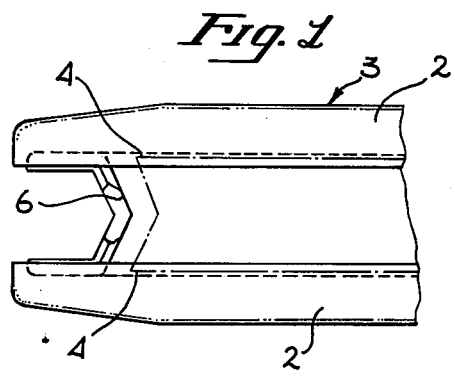
FIG. 1 is a side view of the clip of the present invention in an applicating device.
Figure 2:
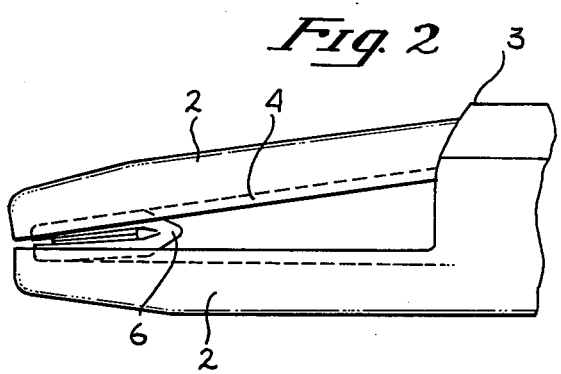
FIG. 2 is a side view of the clip of the present invention in its closed configuration in an applicating device.

Referring to FIG. 1, the hemostatic clip 6 of the present invention is shown in its open configuration as it is disposed in groove 4 in applicating instrument 3. Also shown in FIG. 1 are jaws 2 of the applicating instrument 3. In operation, hemostatic clip 6 is loaded into the extreme end of grove 4 of applicator 3. When the clip 6 is to be used, opposing jaws 2 of applicator 3 close on clip 6, deforming the clip into a closed configuration about a vessel which is to be strangled. In FIG. 2, hemostatic clip 6 is shown in its closed configuration resulting from the squeezing of jaws 2 of applicating instrument 3, thereby causing clip 6 to bend and ultimately collapse.

Figure 3:
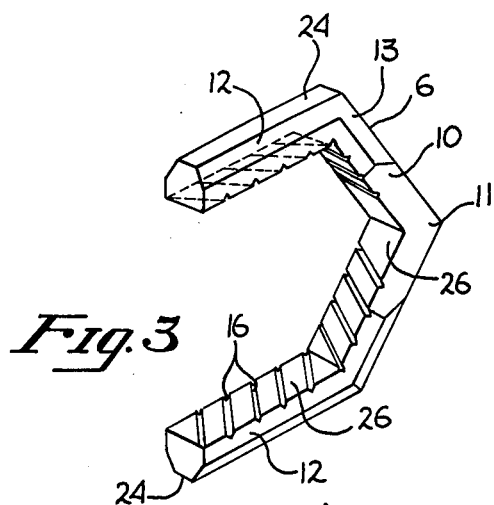
FIG. 3 is a perspective view of the clip.

FIG. 3 is an enlarged view of hemostatic clip 6 in its open configuration. Illustrated here are arm portions 12 as they are coupled to bail portion 10. As is shown in FIG. 3, arm portions 12 are of a generally hexagonal cross-section, having an outwardly facing side 24 and an inwardly facing flat surface 26. Of course, a variety of other configurations may be utilized in the construction of arm portions 12. For example, arm portions 12 may have a generally flat outer side which has cut-away surfaces sloping up and away therefrom so that the outer side is smaller than the remainder of the arm portion. Thus, the cut-away surfaces may be of a rounded configuration or generally flat. However, in the presently preferred embodiment flat surface 26 is the widest side of the hexagonal cross-section while outward facing side 24 is generally parallel to flat surface 26. It can also be seen in FIG.3 that bail portion 10 is generally rectangular at its apex 11, while it assumes the hexagonal cross-sectional shape of arm portions 12 near its extremity 13. Also, in the presently preferred embodiment, apex 11 has a generally sharp exterior surface to provide positive coupling in the applicator device being utilized, while apex 11 is centered between arm portions 12. Diagonally disposed across flat surface 26 are recesses 16.

It can be seen from FIG. 3 that hemostatic clip 6 provides a large surface area of contact when arms 12 are squeezed together, due to the extensive area provided by flat surface 26. This large surface area of contact provides a more sure closure of the vessel since a large area of the vessel being strangled is collapsed against itself. Thus, the possible failure of the clip 6 is greatly minimized. It can also be seen from FIG. 3 that in the presently preferred embodiment arms 12 are essentially of equal length and substantially longer than bail portion 10. The equality of length allows the clip 6 to collapse in a parallel and uniform manner since the outer extremities of each arm are the first to meet during squeezing of clip 6, allowing the more interior surfaces to bend and meet in a uniform manner. The substantial length of each arm 12 is provided in the presently preferred embodiment so as to provide rotational stability of the clip 6 in its applicator device. That is, if each arm 12 was not generally longer than bail portion 10, clip 6 may have a tendency to rotate and become displaced in the applicator device.

Figure 4:
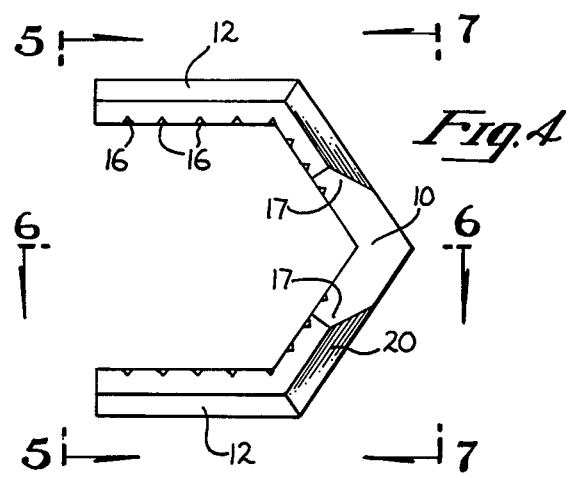
FIG. 4 is a side view of the clip.

FIG. 4 is a side view of hemostatic clip 6, showing the V-shaped cross-section of recesses 16. Also shown in FIG. 4 is the junction 17 of the hexagonal portion 20 of arm portions 12 as they converge on the rectangular cross-sectional area of bail portion 10. Although bail portion 10 is illustrated in FIG. 4 as having a generally V-shaped configuration, of course, it can be of a rounded configuration or a variety of other configurations which are suitably adapted to cooperate with the applicator device being utilized.

Figure 5:
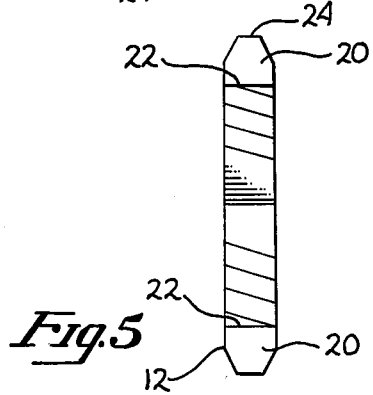
FIG. 5 is a vertical cross-sectional view of the clip taken on the line 5—5 of FIG. 4.
Figure 6:
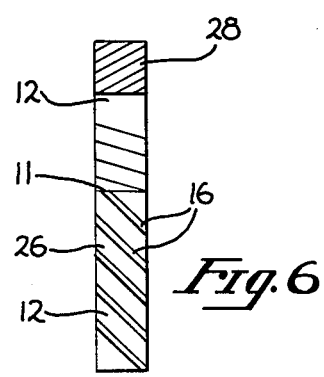
FIG. 6 is a horizontal cross-sectional view of the clip taken on the line 6—6 of FIG. 4.
Figure 7:
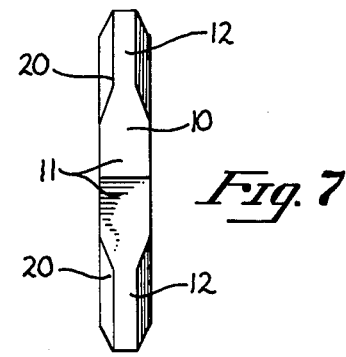
FIG. 7 is a vertical cross-sectional view of the clip taken on substantially the line 7—7 of FIG. 6.

Now referring to FIGS. 5, 6, and 7, three views of the clip illustrated in FIG. 4 are shown. In FIG. 5 an end view of hemostatic clip 6 is shown from a view along line 5—5 of FIG. 4. This view illustrates the hexagonal shape 20 of arm portion 12, and the wide surface 22 of arm portion 12. Also shown in FIG. 5 is outward facing side 24 of arm portion 12. FIG. 6 is a vertical cross-section of FIG. 4 taken along lines 6—6. This FIG. 6 illustrates the rectangular cross-section 28 of bail portion 10 at its apex 11. Also shown is flat surface 26 of arm portion 12 and recesses 16 in both the lower part of arm portion 12 and upper part of arm portion 12. FIG. 7 is a side view of hemostatic clip 6 taken along line 7—7 of FIG. 4. This Figure illustrates the rectangular bail portion 10 as it converges into the hexagonal shape 20 of arm portions 12. In the presently preferred embodiment, apex 11 has a generally flat outwardly facing surface which is substantially normal to the length of the clip 6. This surface provides a sure contact with the feed mechanism of the instrument being used to apply clip 6, although other configurations, such as a concave surface may be used.

Figure 8:
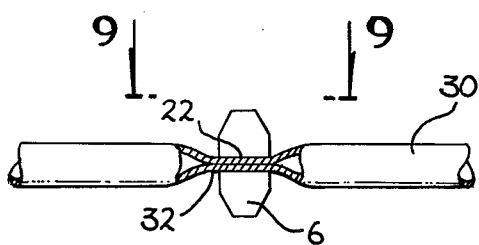
FIG. 8 is a view of the clip as it is closed around a vessel.

FIG. 8 illustrates a blood vessel 30 or similar vessel as it is constricted by hemostatic clip 6. The constricted portions 32 of vessel 30 show opposing walls of the vessel collapsed against one another. It can be seen in FIG. 8 that the flat wide surface 22 of arm portions 12 provide expansive constriction of vessel 30, thereby providing complete and secure strangulation.

Figure 9:
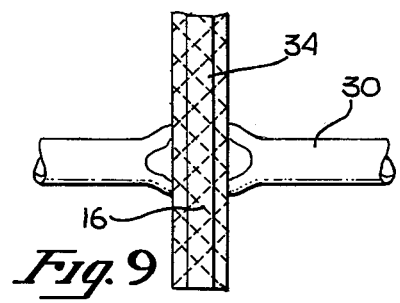
FIG. 9 is a view of the cross-hatched pattern formed by the clip when it is closed about a vessel.

FIG. 9 is a cross-sectional view taken along line 9—9 of FIG. 8. FIG. 9 illustrates collapsed vessel 30 and the resulting configuration of recesses 16 as they are disposed in both the upper part and lower part of arm portions 12. It can be seen from both FIG. 9 and FIG. 3 that recesses 16 are disposed in one arm portion 12 in such a way as to be angularly displaced in relationship to the recesses 16 disposed in the opposing arm portion 12. This angular displacement of recesses 16 results in a cross-hatched pattern 34 when flat surfaces 26 of the opposing arm portions 12 are brought together following closure of clip 6. It is important to note that recesses 16 are all angularly displaced with respect to the length and width of vessel 30. Thus, this cross-hatched configuration 34 will oppose any movement of the clip either in a longitudinal or lateral direction with respect to vessel 30. Therefore, hemostatic clip 6, when it is squeezed around vessel 30, will not have a tendency to slip along the length or width of the vessel.

There has been described herein a new and novel hemostatic clip which has special utility for strangulation of blood vessels and the like. While a specific embodiment of the present invention has been disclosed and described in detail herein, it will be understood by those skilled in the art that various changes in form and detail may be made therein without departing from the spirit and scope of the invention.

We claim:

1. A hemostatic clip formed of elongate deformable material for use in the strangulation of tubular members by means of a hemostatic clip applicator, the clip applicator of the type having jaw portions adapted to receive and maintain hemostatic clips via grooves in said jaws, said jaws further having stop portions at the extremity thereof adapted to maintain said hemostatic clips within said grooves, the hemostatic clip being generally U-shaped and comprising:

(i) a bail portion forming the base of said U-shape;
    (ii) a pair of arms extending from said bail portion and forming the extremities of said U-shape, said arms being separated in a substantially opposed relationship and having opposing substantially flat surfaces, each arm being substantially longer than said bail portion, whereby said substantial length of said arm portions results in stability of said clip in said clip applicator, each arm having a generally trapezoidal cross-section with a narrower outer portion adapted to be received in a respective groove of said clip applicator; and
    (iii) a plurality of spaced parallel diagonally disposed grooves extending downwardly into each of said clip arm opposing surfaces, said grooves extending below each clip arm flat surface and being spaced apart sufficiently so that substantial portions of said flat surface remain between adjacent grooves, the grooves on one arm extending solely in one direction, the grooves on the other arm extending solely in an opposite direction such that the grooves in opposing surfaces are angularly displaced with respect to one another, whereby said grooves form a generally cross-hatched pattern when said opposing substantially flat surfaces are brought into facing contact with one another.

2. The clip of claim 1 wherein said bail portion is V-shaped and each arm is coupled to one extremity of said bail portion.

* * * * *